(12) United States Patent
Belik

(10) Patent No.: US 7,066,012 B1
(45) Date of Patent: Jun. 27, 2006

(54) HARDNESS TESTING DEVICE FOR USE WITH A BICYCLE TIRE

(76) Inventor: Jaroslav Belik, 4955 Sentry Woods La., Pearland, TX (US) 77584

( * ) Notice: Subject to any disclaimer, the term of this patent is extended or adjusted under 35 U.S.C. 154(b) by 73 days.

(21) Appl. No.: 10/834,824

(22) Filed: Apr. 30, 2004

(51) Int. Cl.
*G01N 3/48* (2006.01)

(52) U.S. Cl. .......................................... 73/81

(58) Field of Classification Search ............... 73/81, 73/700
See application file for complete search history.

(56) References Cited

U.S. PATENT DOCUMENTS

| | | | |
|---|---|---|---|
| 1,658,661 A | * | 2/1928 | Trewhella ................... 73/81 |
| 1,875,862 A | * | 9/1932 | Fair ............................. 73/81 |
| 4,120,614 A | | 10/1978 | Bouder |
| 4,331,026 A | * | 5/1982 | Howard et al. ............. 73/81 |
| 4,348,891 A | | 9/1982 | Stickler |
| 4,919,600 A | | 4/1990 | Yang |
| 5,503,012 A | | 4/1996 | Rabizadeh |
| 5,533,405 A | * | 7/1996 | Hoshino .................... 73/760 |
| 5,964,577 A | | 10/1999 | Chuang |
| 6,132,189 A | | 10/2000 | Ward |
| 6,196,807 B1 | | 3/2001 | Wu |
| 6,558,129 B1 | | 5/2003 | Wang |

* cited by examiner

Primary Examiner—Charles Garber
(74) Attorney, Agent, or Firm—Egbert Law Offices

(57) ABSTRACT

A hardness testing device for a bicycle tire has a body with a surface thereon, an arm having a protrusion extending outwardly of the surface, a spring cooperative with a portion of the arm for resisting movement of the protrusion inwardly of the body when the protrusion contacts a surface of the tire, and an indicator cooperative with the arm for providing a humanly perceivable indication of movement of the protrusion relative to a hardness of the tire. The arm is pivotally mounted in or on the body.

12 Claims, 4 Drawing Sheets

HARDNESS TESTING DEVICE FOR USE WITH A BICYCLE TIRE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to devices for testing the inflation of a bicycle tire. More particularly, the present invention relates to devices for testing the hardness of an inflated tire. Additionally, the present invention relates to tire hardness testing devices that do not attach to the air-admitting valve of the bicycle tire.

BACKGROUND OF THE INVENTION

Virtually all bicycles are equipped with pneumatically-inflated tires. Conventionally, these tires are inflated by attaching a pump to an air-admitting valve secured to the inner tube of the tire. When the tire pump is manually activated, air will pass from the tire pump, through the valve, and into the inner tube. Conventional hand-held bicycle tire pumps are often very cumbersome in the inflation of the tire. As high pressures are received within the interior of the tire, it becomes increasingly difficult to pump the manual tire pump so as to achieve the desired pressures. Modern bicycle tires often require pressures in excess 100 p.s.i. in order to obtain the desired hardness. The application of the proper forces onto the tire pump can often be very exhausting to the cyclist.

In order to achieve the optimum bicycle tire inflation pressure, the cyclist will repeatedly increase the amount of pressure within the tire. If the amount of pressure within the inner tube of the tire should fall below a desired level, then the tire will be too flat for proper usage on the road. Optimum peddling efficiency deteriorates when there is too little pressure within the tire. As a result, the cyclist will inefficiently pump the pedals of the bicycle in order to propel himself or herself along the bicycle pathway.

In other circumstances, it is not desirable to have an excess amount of inflation pressure within the tire. If too much pressure was received within the tire, then there is the risk of bursting the tire. Additionally, excess inflation will reduce friction between the surface of the tire and the road. This reduced friction will enhance the risks of sliding and hydroplaning and will reduce traction. As a result, most bicycle tires are provided with recommended inflation pressures in a desired range.

Heretofore, the only effective technique for determining the amount of pressure within the tire is the application of tire pressure gauges. These tire pressure gauges are similar to those used on automotive tires. The bicycle tire pressure gauge includes an inlet valve that is secured over the tire valve so that a small amount of air will pass into the gauge. The gauge will then suitably react so as to provide a visual indication to the user to the amount of pressure within the tire. If there is too little pressure within the tire, then the cyclist must, once again, pump the tire to the desired pressure. It is typical that a small amount of pressure will continually leak from the tire during continued use or over extended periods of time.

Unfortunately, whenever the tire pressure gauge is applied to the valve of the tire, there is a risk that a large amount of pressure is lost. Most cyclists have experienced the frustrating problem where the pressure in the tire is lost because of an inadequate application of the tire pressure gauge to the valve of the tire. Often, an excess amount of the air will leak from the tire during the application of the pressure gauge onto the tire valve. So as to accommodate this problem, cyclists often will attempt to overinflate the tire so as to accommodate the small amount of leakage that will occur when the pressure is being measured. In many circumstances, cyclists will resist the need to continually monitor tire pressure in order to avoid the accidental loss of pressure from the tire. The pumping of the tire is considered a very undesirable activity by the cyclist.

In the past, various U.S. patents have issued relating to bicycle tire pressure gauges. For example, U.S. Pat. No. 5,505,012, issued on Apr. 2, 1996, to Rabizadeh, discloses a tire pressure monitoring device that includes a ball disposed within a tube which has an opening, at one end, in communication with the interior of the tire. The tube has a transparent window along its length to allow the position of the tire pressure ball to be visualized. The transparent window has graduations calibrated to allow the tire pressure to be determined by the position of the ball.

U.S. Pat. No. 4,919,600, issued on Apr. 24, 1990 to Yang, discloses a tire pump with a pressure gauge including a cylinder having a piston head slidably provided in the cylinder. A pressure measuring device with a pressure indicating element is disposed at a front end of the cylinder so that the pressure indicating element is readable through a peep hole in the cylinder. The pressure measuring device interconnects at an outlet of the cylinder. A bypass tube with a check valve is disposed beside the pressure measuring device so that air pressurized by the piston head blows out from the outlet through the bypass tube. The pressurized air also flows through the air holes in order that the pressure within the pumped tire can be read from the pressure indicating element of the pressure measuring device through the peep hole.

U.S. Pat. No. 6,196,807, issued on Mar. 6, 2001 to S. Wu, describes a pressure gauge of a tire pump which includes a chamber and a pressure indicator movably received in the chamber. The pressure indicator has a tube with a head portion attached to a first end thereof and a receptacle defined in a second end thereof. The head portion is in slidable contact with an inner periphery of the chamber and the tube is not in contact with the inner periphery of the chamber.

U.S. Pat. No. 6,132,189, issued on Oct. 17, 2000 to A. R. Ward, teaches a combined bicycle tire and air suspension pump with a removable pressure gauge. U.S. Pat. No. 6,558,129, issued on May 6, 2003 to L. P. Wang, also discloses an air pump having a pressure gauge thereon. Similarly, U.S. Pat. No. 4,120,614, issued on Oct. 17, 1978 to P. C. Bouder, discloses a hand bicycle pump with a pressure preselection and a display means. Additionally, and furthermore, U.S. Pat. No. 5,964,577, issued on Oct. 12, 1999 to L. Chuang, discloses a hand air pump with a pivotable pressure gauge.

In the field of tire hardness testers, there is provided a patent relating to the testing of automotive tires in the form described in U.S. Pat. No. 4,348,891 of Sep. 14, 1982. This patent describes a tire hardness tester wherein a support member movably supports a durometer which is connected to means for controlling the rate of the descent of such a durometer to provide a constant predetermined force for measuring the hardness of a tire tread. A tire supports the tire in such way that it is in alignment with the durometer.

It is an object of the present invention to provide a bicycle tire hardness testing device that is a simple and easy technique for checking on the correct hardness of the tire.

It is another object of the present invention to provide a bicycle tire hardness testing device which is small, light and easy to transport.

It is another object of the present invention to provide a bicycle tire hardness testing device which correlates with the pressure in the tire without the need for using a pressure gauge secured to the inflation valve of the tire.

It is another object of the present invention to provide a bicycle tire hardness device which is of greater reliability than conventional valve-connected devices.

It is a further object of the present invention to provide a bicycle tire hardness testing device which is easy to manufacture and relatively inexpensive.

These and other objects and advantages of the present invention will become apparent from a reading of the attached specification and appended claims.

BRIEF SUMMARY OF THE INVENTION

The present invention is a hardness testing device for bicycle tires which comprises a body, an arm having a protrusion extending outwardly of a surface of the body, a spring means cooperative with a portion of the arm for resisting movement of the protrusion inwardly of the body when the protrusion contacts a surface of the tire, and an indicator cooperative with the arm. The indicator provides a humanly-perceivable indication of a movement of the protrusion relative to a hardness of the tire. The arm is pivotally mounted in or on the body.

In particular, the body has an arcuate surface generally matching the curvature of the tire. This surface of the body has an indentation formed thereon. The protrusion extends outwardly of this indentation. The body has a first channel formed interior thereof. The arm is pivotally mounted within this channel so as to pivot with respect to a pivot point. The spring means acts on side of the pivot point. The protrusion is positioned on an opposite side of the pivot point. The arm has a portion extending outwardly of another surface of the body. The indicator is an indicia on the body adjacent to the portion of the body. The indicia is an arrow adjustably affixed onto the body adjacent another surface of the body. The arrow is indicative of a desired hardness of the bicycle tire. The body has a second channel formed therein. The spring is positioned in this second channel.

In the present invention, the spring has an end extending outwardly of the second channel so as to contact the arm. A screw is threadedly secured to the second channel. The spring is affixed to the screw. The screw is adjustable so as to adjust an urging force of the spring upon the arm.

In the alternative form of the present invention, the indicator is a limit switch which extends into the body. An alarm is positioned in the body and connected to the limit switch so as to activate an alarm when the arm contacts the limit switch. The alarm can either be a light affixed to the body and connected to the limit switch or a loudspeaker affixed to the body and connected to the limit switch.

In another alternative form of the present invention, the body has a first channel formed therein. The arm is an elongated member having an end pivotally mounted adjacent to one end of the body in the channel. The protrusion extends transversely to the elongated member. The indicator is at an opposite end of the elongated member. This opposite end of the elongated member extends outwardly of an opposite end of the body. In this form of the present invention, the body has a second channel extending transversely to the first channel. The spring is received in the second channel for acting on a surface of the elongated member away from the pivotal mounting of the end of the elongated member. The spring includes a compression member received within the second channel. The compression member has an end contacting the surface of the elongated member. A threaded member is threadedly received in the second channel. The threaded member is adjustably connected to the compression member so as to adjust a compression exerted by the compression member on the surface of the arm. The compression member is a piston that is slidably received in the threaded member and slidably movable in the second channel. The compression member also includes a spring interposed between the piston and the threaded member so as to urge on the piston. The threaded member has a head affixed to an end thereof and positioned outwardly of the body.

In still another alternative embodiment of the present invention, the arm extends generally transverse to the surface of the body. The protrusion extends outwardly from an end of the arm. The spring urges on an end of the arm opposite the protrusion. The arm has a notch formed therein. The indicator is a pointer pivotally mounted in the body. This pointer has an end received within the notch. The indicator also includes a scale affixed to the body adjacent an end of the pointer opposite the notch. The arm is movable such that the notch causes the pointer to pivot an end of the pointer so as to move relative to the scale. The spring includes a threaded member threadedly received within a channel of the body. The spring has an end received by the threaded member and an opposite end urging on the arm. The threaded member is adjustably positioned so as to vary an urging force by the spring upon the arm.

DETAILED DESCRIPTION OF THE INVENTION

Figure 1:
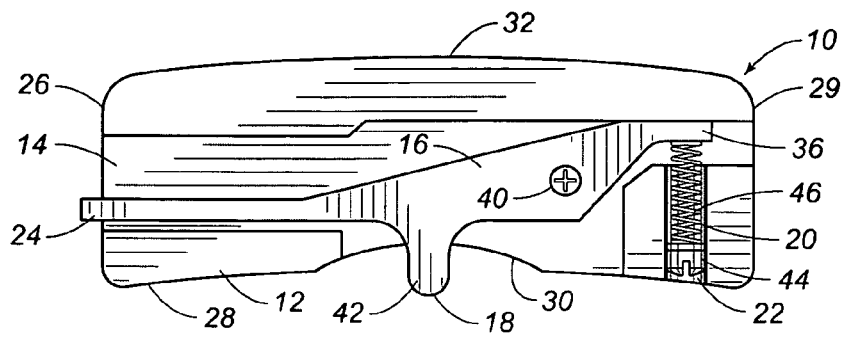
FIG. 1 is a transparent side elevational view of the preferred embodiment of the tire hardness testing device of the present invention.

Referring to FIG. 1, there is shown the bicycle tire hardness testing device 10 in accordance with the preferred embodiment of the present invention. The bicycle tire hardness testing device 10 includes a body 12 having a channel 14 formed therein, an arm 16 having a protrusion 18 extending outwardly therefrom, a spring means 20 positioned within a second channel 22 of the body 12, and an indicator 24 extending outwardly of a side 26 of the body 12.

In the present invention, the body 12 can be formed of a steel or a plastic material. The body 12 includes a surface 28 having a curvature generally matching the curvature of the tire upon which the testing device 10 is applied. An indentation 30 is formed in the surface 28 generally at the area of the protrusion 18 of arm 16. As can be seen, the protrusion 18 will extend outwardly from the interior of the body 12 and outwardly of the surface 28. As such, the protrusion 18 is illustrated as in a proper position for contacting the surface of a bicycle tire when the surface 28 is applied thereto. The body 12 also includes sides 26 and 29 and a top surface 32. The body 12 should be suitably configured for easy grasping and gripping. The top surface 32 should be a generally curved ergonomic surface which allows the user's hand to apply downward forces thereon. The channel 14 has one end opening at side 26 of body 12. The channel 22 is formed in the body 12 so as to generally extend transversely to the channel 14. Channel 22 is suitable for receiving the spring means 20 therein.

The arm 16 includes an elongate portion 34 extending through the channel 14. The elongate portion 34 has a terminal end 36 positioned generally adjacent to the side 29 of body 12. The opposite end of the arm 16 will extend outwardly of the side 26 of body 12 so as to be the indicator 24 for the bicycle tire hardness tester 10 of the present invention. The arm 16 is pivotally mounted within the channel 14 of body 12 about pivot point 40. End 36 is at one side of pivot point 40. Indicator 24 is on the opposite side of pivot point 40. The protrusion 18 will extend transversely outwardly from the elongated portion 34 on the side of pivot point 40 opposite the end 36. The spring means 20 acts on a surface of the elongate portion 34 adjacent to the end 36.

As can be seen in FIG. 1, the protrusion 18 has a generally curved bottom edge 42. The bottom edge 42 will be suitable for contacting the tread of the bicycle tire. As shown in FIG. 1, the indicator 24 of the arm 16 is at its lowered position within the channel 14 at side 26 of body 12. In this position, the spring means 20 is urging upon the surface adjacent to end 36 of arm 16 against the inner wall of the channel 14. The position of the indicator 24 is at a lower position so as to indicate that no force has been applied to the bottom edge 42 of protrusion 18.

In FIG. 1, it can be seen that the spring means 20 is affixed within the channel 22. A threaded member 44 is threadedly received within the channel 22. A compression spring 46 is mounted on the threaded member 44. Threaded member 44 can be suitably adjusted so as to adjust an urging force of the compression spring 46 upon the surface of the end 36 of arm 16. As such, the amount of force required to contact the bottom edge 42 of protrusion 18 so as to move the indicator 24 from its lowered position (as shown in FIG. 1) to a raised position (as shown in FIG. 3) can be adjusted by rotating the threaded member 44, as desired.

Figure 2:
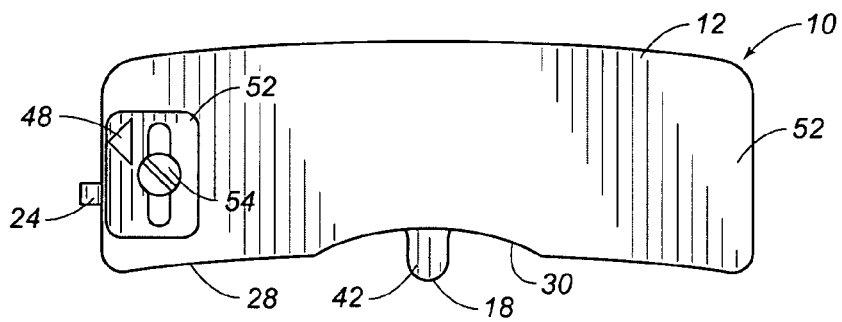
FIG. 2 is a side non-transparent view of the tire hardness testing device of the present invention.

In FIG. 2, it can be seen that the indicator 24 also includes an arrow 48 which is mounted on a slide plate 50 on the outer surface 52 of body 12. A screw 54 can be rotated so as to loosen the slide plate 50 so that the arrow 48 can be moved to another position, as desired. As such, when the desired bicycle hardness is achieved through the pumping of the tire, and the testing device 10 is applied to the surface of the tire, the arrow 48 can be suitably adjusted to match the position of the indicator 24 so that the desired hardness of the tire can always be ascertained. In FIG. 2, it can also be seen that the protrusion 18 has its bottom edge 42 extending outwardly of the indentation 30 formed on the surface 28 of body 12.

Figure 3:
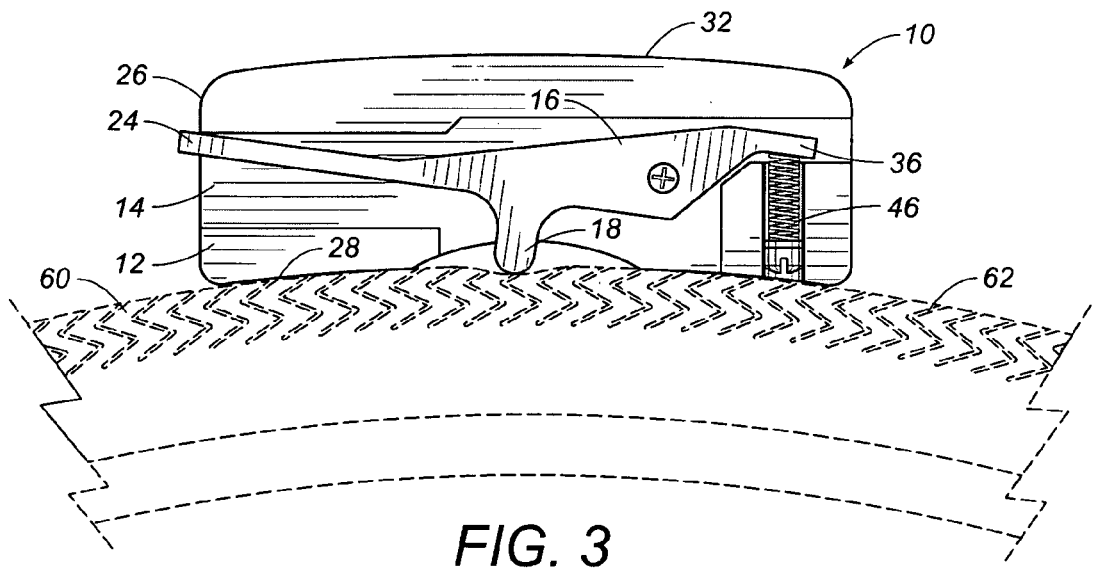
FIG. 3 is a side elevational view showing the application of the tire hardness testing device upon a bicycle tire.

FIG. 3 shows the application of the device 10 to bicycle tire 60. Bicycle tire 60 is illustrated as having tread 62 formed thereon. The device 10 is applied to the tread 62 of bicycle tire 60 so that the surface 28 of body 12 is in surface-to-surface contact with the tread 62. A downward force is hand-applied onto the top surface 32 of the device 10. The hardness of the tire 60 will cause the protrusion 18 to suitably deflect and overcome the resistance on the end 36 of arm 16 as caused by compression spring 46. As a result, the indicator 24, extending outwardly of the side 26 of body 12, would move upwardly within the channel 14. In this position, as aligned with the arrow 48, the device 10 will indicate that the tire 60 has the desired inflation. If upon application to the tire 60, the indicator 24 does not rise to the level of the arrow 48, then the device 10 will be indicative of inadequate or low pressures. As a result, the pressurization of the tire can be ascertained without the need for the application of a tire pressure gauge onto the valve of the tire.

Figure 4:
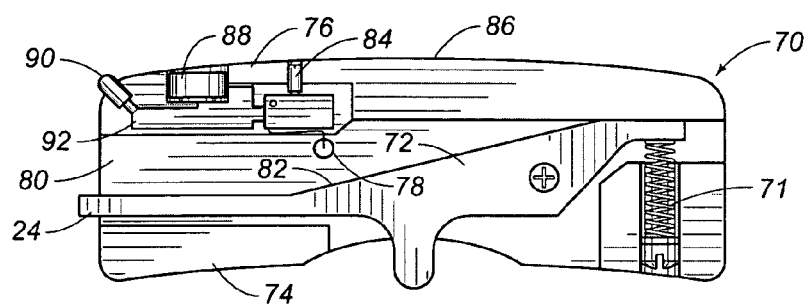
FIG. 4 is a side transparent elevational view of a first alternative embodiment of the tire hardness testing device of the present invention.
Figure 5:
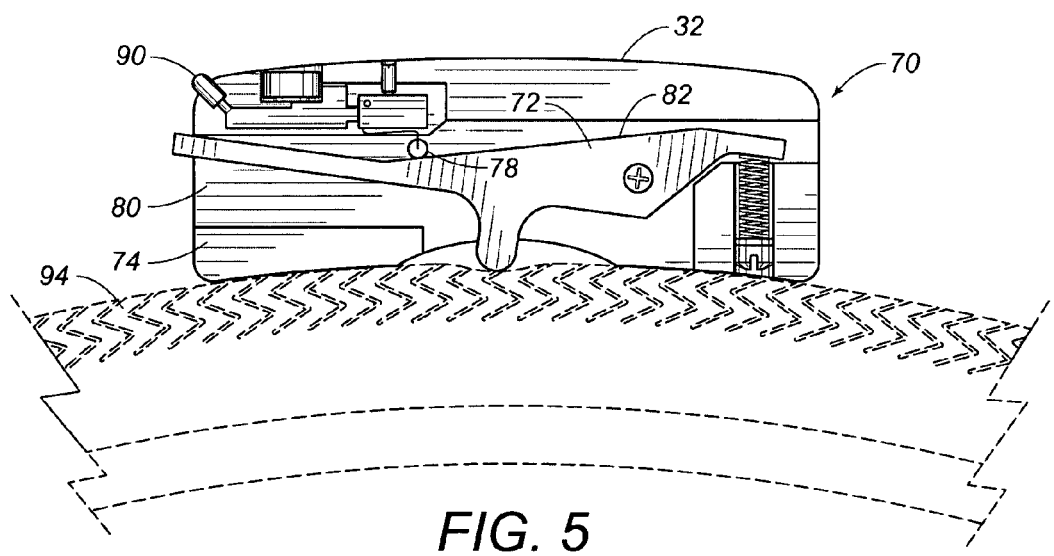
FIG. 5 is a transparent side elevational view of the first alternative embodiment of the tire hardness testing device of the present invention as illustrated as applied to a bicycle tire.

FIG. 4 shows an alternative form of a tire testing device 70 in accordance with the present invention. Testing device 70 also includes an arm 72 as mounted within body 74. Arm 72 and body 74 have a similar configuration to the arm 16 and the body 12 of the embodiment of FIGS. 1–3. Similarly, the spring 71 is of a similar configuration to that of the prior embodiment. The important difference of the embodiment shown in FIG. 4 is the application of an alarm mechanism 76 within the body 74. The alarm mechanism 76 includes a limit switch 78 which extends into the channel 80 in the body 74. Limit switch 78 is in a position for contacting a surface 82 of the arm 72. The position of the limit switch 78 can be adjusted by moving the set screw 84 which opens at the top surface 86 of body 74. A battery 88 is also accessible through the top surface 86 so as to provide power to the limit switch 78 and to a light 90 extending outwardly of the top surface 86 of body 74. Wiring 92 extends between the processor associated with limit switch 78 and the battery 88 so as to interconnect the battery 88 in selective contact with the light 90. In FIG. 5, it can be seen that the device 70 is applied to the tire 94. This causes the arm 72 to move upwardly within the channel 80 of body 74. As a result, the surface 92 contacts the limit switch 78. This will activate the light 90 so as to provide a visual indication to the user of the device 70 that the desired inflation of the tire 94 has been achieved.

Figure 6:
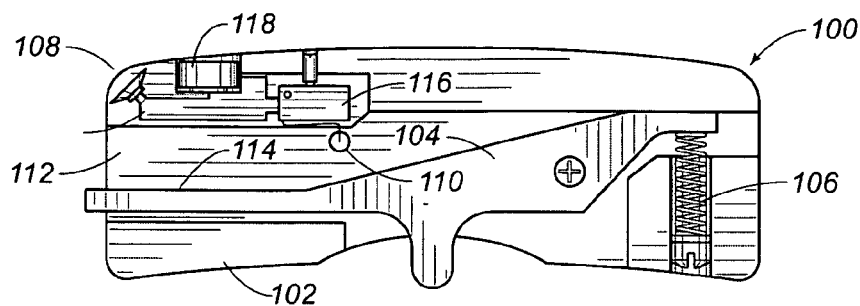
FIG. 6 is a transparent side elevational view of a second alternative embodiment of the tire hardness testing device of the present invention.
Figure 7:
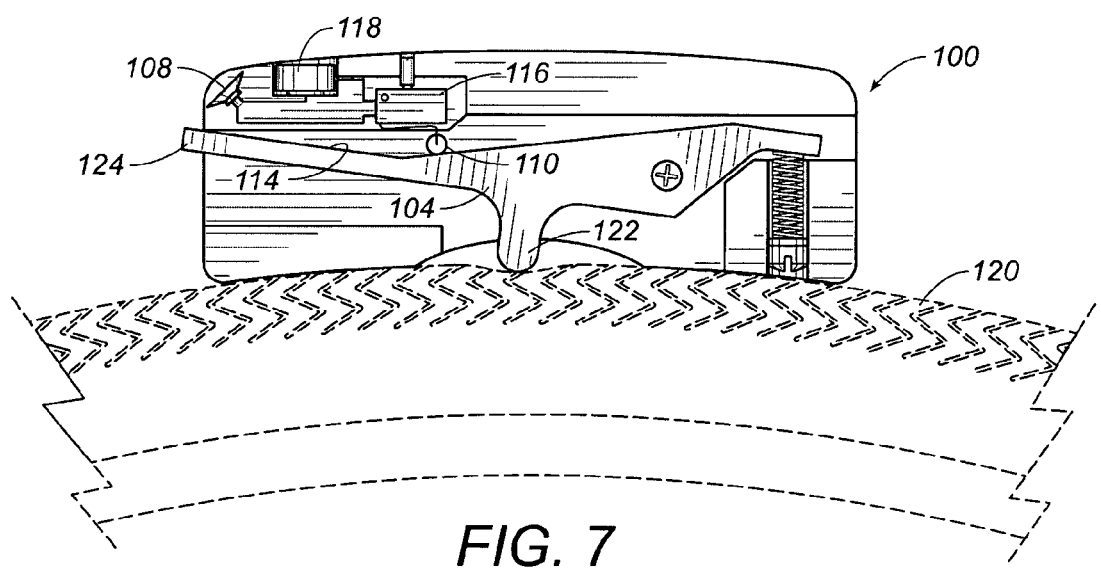
FIG. 7 is a transparent side elevational view of the tire hardness testing device of the second embodiment of the present invention as applied to a bicycle tire.

Referring to FIG. 6, the tire hardness testing device 100 of a second alternative form of the present invention is particularly illustrated. The body 102 and the arm 104 have a configuration similar to that as shown in FIGS. 1–3. Similarly, the spring 106 has a configuration similar to that of the previous embodiment. The important difference between the tire hardness testing device 100 of the second alternative embodiment is the use of a sound-emitting loudspeaker 108. As can be seen, a limit switch 110 (of a type similar to that shown in FIGS. 4 and 5) is positioned within the channel 112 of the body 102. The limit switch 110 is positioned so as to be activated by contact with the surface 114 of arm 104. A processor 116 is connected to the limit switch 110 so as to activate the loudspeaker 108 and to connect the battery 118 thereto when a contact is made between the surface 114 and the limit switch 110. FIG. 7 specifically illustrates the process of sound emission when the tire 120 acts on the protrusion 122 of arm 104 so as to bring surface 114 into contact with the limit switch 110. When the hardness of the tire 120 is sufficient so as to move the indicator portion 124 into an upper position, contact is made with the limit switch 110 which will transmit a signal from processor 116 and power from battery 118 so as to emit a sound from loudspeaker 108.

Figure 8:
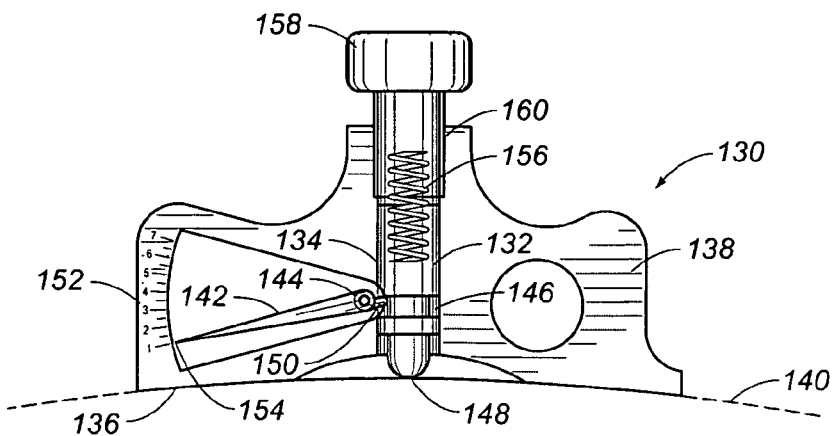
FIG. 8 is a third alternative embodiment, as shown in transparent side elevation view, of the tire hardness testing device of the present invention.

FIG. 8 shows a third alternative embodiment 130 of the device of the present invention. Unlike the previous embodiment, the arm 132 extends through a channel 134 arranged generally transverse to the bottom surface 136 of the body 138. Surface 136 has a curvature which generally matches the curvature of the tire 140. The indicator 142 is in the form of a pointer having a pivot point 144 generally adjacent to the arm 132. In particular, the arm 132 includes a notch 146 formed around a periphery thereof. The protrusion 148 will extend outwardly from the arm 132. In the embodiment of the device 130 of FIG. 8, the protrusion 148 will be in longitudinal alignment with the arm 132. The indicator 142 has a finger 150 which is received within the notch 146. A scale 152 is formed on a periphery of the body 138 generally adjacent to the end 154 of the indicator 142.

The spring mechanism 156 of the device 130 includes a head 158 which is connected to a threaded member 160. This spring mechanism 156 is received within the threaded member 160 so as to exert a resilient force against the arm 132. The head 158 can be suitably rotated so as to adjust the amount of compression caused by the spring mechanism 156 upon the arm 132. When the device 130 is applied against the surface of the tire 140, the notch 146 on arm 132 will cause the indicator 142 to pivot about pivot point 144. As a result, the end 154 will move relative to the location of the various marking on the scale 152 so as to indicate the amount of hardness of the tire 140.

Figure 9:
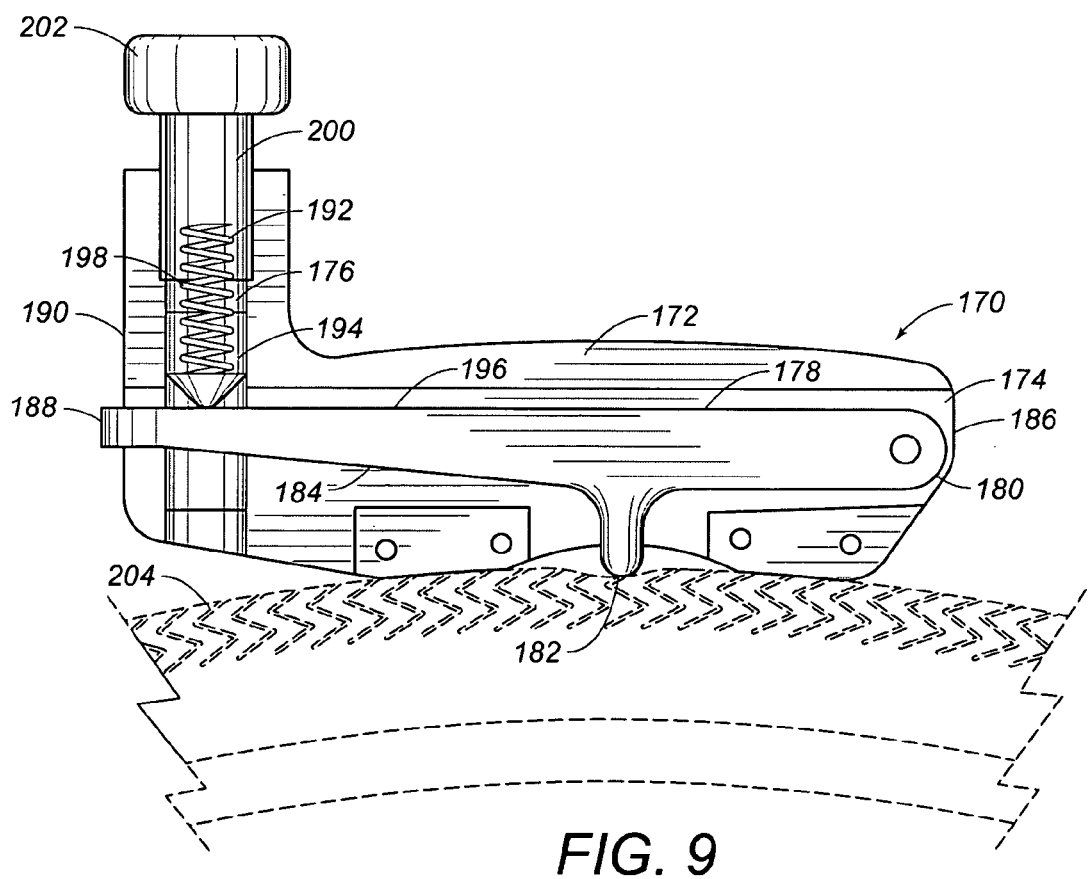
FIG. 9 is a transparent side elevational view of the application of a fourth alternative embodiment of the bicycle tire hardness testing device of the present invention as applied upon a bicycle tire.

FIG. 9 is another alternative embodiment 170 of the tire hardness testing device of the present invention. The device 170 includes a body 172 having a channel 174 extending therethrough. A second channel 176 will extend in generally transverse relationship to the first channel 174. The arm 178 is pivotally mounted at a pivot point 180 within the channel 174. A protrusion 182 will extend transversely outwardly from the elongate member 184 of arm 178. The pivot point 180 is located in proximity to the end 186 of the body 172. The elongate member 184 has an end 188 which extends outwardly of the end 190 of the body 172.

In FIG. 9, it can be seen that the spring mechanism 192 is received within a piston 194. The piston 194 has an end abutting the top surface 196 of the elongate member 184 of arm 178. The spring mechanism 192 also includes a compression spring 198 received within the threaded member 200. A head 202 extends outwardly of the body 172 and secured to the threaded member 200. The head 202 is suitably rotatable so as to adjust the amount of compression forces exerted by the spring 198 upon the piston 194. As a result of this configuration, when the protrusion 182 contacts the surface of a tire 204, the arrangement of the compression mechanism 192 will resist the upward movement of the indicator 188 of the elongate member 184 of arm 178. If the pressure in the tire 204 is sufficient, then the force will cause the indicator 188 to move to a desired location indicative of sufficient pressure.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A hardness testing device for a tire comprising:
   a body having a surface thereon;
   an arm having a protrusion extending outwardly of said surface, said arm mounted in or on said body;
   a spring means cooperative with a portion of said arm, said spring means for resisting movement of said protrusion inwardly of said body when said protrusion contacts a surface of the tire; and
   an indicator means cooperative with said arm, said indicator means for providing a humanly perceivable indication of a movement of said protrusion relative to a hardness of the tire, said surface of said body being an arcuate surface generally matching a curvature of the tire.

2. A hardness testing device for a tire comprising:
   a body having a surface thereon;
   an arm having a protrusion extending outwardly of said surface, said arm mounted in or on said body;
   a spring means cooperative with a portion of said arm, said spring means for resisting movement of said protrusion inwardly of said body when said protrusion contacts a surface of the tire; and
   an indicator means cooperative with said arm, said indicator means for providing a humanly perceivable indication of a movement of said protrusion relative to a hardness of the tire, said surface of said body having an indentation formed thereat, said protrusion extending outwardly of said indentation.

3. The device of claim 2, said body having a first channel formed interior thereof, said arm pivotally mounted within said channel so as to pivot with respect to a pivot point, said spring means acting on one side of said pivot point, said protrusion positioned on an opposite side of said pivot point.

4. The device of claim 3, said arm having a portion extending outwardly of another surface of said body, said indicator means being an indicia on said body adjacent said portion of said arm.

5. The device of claim 4, said indicia being an arrow adjustably affixed onto said body adjacent said another surface of said body, said arrow being indicative of a desired hardness of the tire.

6. The device of claim 3, said body having a second channel formed therein, said spring means positioned in said second channel.

7. The device of claim 6, said spring means comprising:
   a spring having an end extending outwardly of said second channel so as to contact said arm; and
   a screw threadedly received in said second channel, said spring being affixed to said screw, said screw being adjustable so as to adjust an urging force of said spring against said arm.

8. A hardness testing device for a tire comprising:
   a body having a surface thereon;

an arm having a protrusion extending outwardly of said surface, said arm mounted in or on said body;
a spring means cooperative with a portion of said arm, said spring means for resisting movement of said protrusion inwardly of said body when said protrusion contacts a surface of the tire; and
an indicator means cooperative with said arm, said indicator means for providing a humanly perceivable indication of a movement of said protrusion relative to a hardness of the tire, said indicator means comprising:
  a limit switch extending into said body; and
  an alarm means positioned on said body for activating an alarm when said arm contacts said limit switch.

9. The device of claim 8, said alarm means comprising:
a light affixed to said body and connected to said limit switch.

10. The device of claim 8, said alarm means comprising:
a loudspeaker affixed to said body and connected to said limit switch.

11. A hardness testing device for a tire comprising:
a body having a surface thereon;
an arm having a protrusion extending outwardly of said surface, said arm mounted in or on said body;
a spring means cooperative with a portion of said arm, said spring means for resisting movement of said protrusion inwardly of said body when said protrusion contacts a surface of the tire; and
an indicator means cooperative with said arm, said indicator means for providing a humanly perceivable indication of a movement of said protrusion relative to a hardness of the tire, said body having a first channel formed therein, said arm being an elongate member having an end pivotally mounted adjacent one side of said body in said channel, said protrusion extending transversely to said elongate member, said indicator means being an opposite end of said elongate member, said opposite end of said elongate member extending outwardly of an opposite side of said body.

12. The device of claim 11, said body having a second channel extending transversely to said first channel, said spring means received in said second channel for acting on a surface of said elongate member away from the pivotally mounted end of said elongate member.

* * * * *